United States Patent
Hoffman

(10) Patent No.: US 11,786,496 B2
(45) Date of Patent: Oct. 17, 2023

(54) COMPOSITION AND METHODS FOR TREATING INTESTINAL HYPERPERMEABILITY

(71) Applicant: Yamo Pharmaceuticals LLC, New York, NY (US)

(72) Inventor: Steven Hoffman, Mahwah, NJ (US)

(73) Assignee: YAMO PHARMACEUTICALS LLC, New York, NY (US)

( * ) Notice: Subject to any disclaimer, the term of this patent is extended or adjusted under 35 U.S.C. 154(b) by 151 days.

(21) Appl. No.: 17/096,761

(22) Filed: Nov. 12, 2020

(65) Prior Publication Data

US 2021/0137868 A1 May 13, 2021

Related U.S. Application Data

(63) Continuation of application No. 16/693,589, filed on Nov. 25, 2019, now Pat. No. 10,857,118, which is a continuation of application No. 16/112,879, filed on Aug. 27, 2018, now Pat. No. 10,517,845, which is a continuation of application No. 15/695,327, filed on Sep. 5, 2017, now Pat. No. 10,085,959, which is a continuation of application No. 15/138,733, filed on Apr. 26, 2016, now Pat. No. 9,757,348, which is a continuation of application No. 14/520,116, filed on Oct. 21, 2014, now Pat. No. 9,326,962, which is a continuation-in-part of application No. 14/062,165, filed on Oct. 24, 2013, now abandoned.

(60) Provisional application No. 61/894,261, filed on Oct. 22, 2013.

(51) Int. Cl.
| | |
|---|---|
| A61K 31/198 | (2006.01) |
| A61K 31/4166 | (2006.01) |
| A61K 9/00 | (2006.01) |
| A61K 31/19 | (2006.01) |
| A61K 31/55 | (2006.01) |
| A61K 45/06 | (2006.01) |

(52) U.S. Cl.
CPC .......... *A61K 31/198* (2013.01); *A61K 9/0019* (2013.01); *A61K 9/0053* (2013.01); *A61K 31/19* (2013.01); *A61K 31/4166* (2013.01); *A61K 31/55* (2013.01); *A61K 45/06* (2013.01)

(58) Field of Classification Search
CPC .................................................. A61K 31/198
See application file for complete search history.

(56) References Cited

U.S. PATENT DOCUMENTS

| | | |
|---|---|---|
| 4,117,161 A | 9/1978 | Pozuelo |
| 4,165,382 A | 8/1979 | Pozuelo |
| 4,189,604 A | 2/1980 | Umezawa et al. |
| 4,240,975 A | 12/1980 | Umezawa et al. |
| 5,073,541 A | 12/1991 | Taylor et al. |
| 5,206,018 A | 4/1993 | Sehgal et al. |
| 5,225,435 A | 7/1993 | Pawelek et al. |
| 5,576,290 A | 11/1996 | Hadley |
| 5,674,839 A | 10/1997 | Hruby et al. |
| 5,683,981 A | 11/1997 | Hadley et al. |
| 5,714,576 A | 2/1998 | Hruby et al. |
| 6,359,001 B1 | 3/2002 | Drago |
| 7,452,868 B2 | 11/2008 | Kuzma et al. |
| 9,308,188 B2 * | 4/2016 | Hoffman ................. A61K 31/19 |
| 9,326,962 B2 * | 5/2016 | Hoffman ............... A61K 9/0053 |
| 9,757,348 B2 * | 9/2017 | Hoffman ............ A61K 31/4166 |
| 10,085,959 B2 * | 10/2018 | Hoffman ............... A61K 9/0019 |
| 10,517,845 B2 * | 12/2019 | Hoffman ............... A61K 31/198 |
| 10,857,118 B2 * | 12/2020 | Hoffman ............... A61K 9/0053 |
| 2002/0128304 A1 | 9/2002 | DAmato |
| 2003/0059471 A1 | 3/2003 | Compton et al. |
| 2006/0063699 A1 | 3/2006 | Larsen |
| 2006/0122181 A1 | 6/2006 | Ikemoto et al. |
| 2009/0030067 A1 | 1/2009 | Wosikowski-Buters et al. |
| 2010/0216781 A1 | 8/2010 | Perrin-Ninkovic et al. |
| 2013/0183263 A1 | 7/2013 | Hoffman |
| 2013/0243873 A1 | 9/2013 | Aversa et al. |
| 2015/0111937 A1 | 4/2015 | Hoffman |
| 2015/0216827 A1 | 8/2015 | Hoffman |

FOREIGN PATENT DOCUMENTS

| | | |
|---|---|---|
| JP | 54062325 A | 5/1979 |
| JP | 2008515801 A | 5/2008 |
| WO | 0178704 A2 | 10/2001 |
| WO | 02/100885 A2 | 12/2002 |
| WO | 2009054001 A1 | 4/2009 |
| WO | 2009109649 A1 | 9/2009 |
| WO | 2009131631 A1 | 10/2009 |
| WO | 2010022243 A1 | 2/2010 |
| WO | 2010118419 A2 | 10/2010 |
| WO | 2011112576 A1 | 9/2011 |
| WO | 2012123819 A1 | 9/2012 |
| WO | 2012165984 A1 | 12/2012 |
| WO | 2015061328 A3 | 4/2015 |

OTHER PUBLICATIONS

Bloemen et al., Challenge and Therapeutic Sutdies Using Alpha-Methyl-para-Tyrosine (AMPT) in Neuropsychiatric Disorders: A Review; Central Nervous System Agents in Medicinal Chemistry, vol. 8, No. 4, Dec. 2008 [Cited in related U.S. Appl. No. 15/695,327].

(Continued)

*Primary Examiner* — Rei Tsang Shiao
(74) *Attorney, Agent, or Firm* — BAKERHOSTETLER

(57) ABSTRACT

The present invention provides methods, compositions, and kits for treating intestinal hyperpermeability in a subject in need thereof, including conditions such as hyperglycemia and underlying diseases such as diabetes, autism, fibromyalgia, inflammatory bowel disease (IBD), graft versus host disease (GVHD), HIV/AIDS, multiple organ dysfunction syndrome, irritable bowel syndrome (IBS), celiac disease, eczema, psoriasis, acute pancreatitis, Parkinson's disease, depression, chronic fatigue syndrome, asthma, multiple sclerosis, arthritis, ankylosing spondylitis, nonalcoholic fatty liver disease, alcoholic cirrhosis, environmental enteropathy, or kwashiorkor.

13 Claims, No Drawings

(56) References Cited

OTHER PUBLICATIONS

Boni et al., "Radioiodine-labelled alpha-methyl-tyrosine in malignant melanoma: cell culture studies and results in patients", British Journal of Dermatology, Jul. 1997, vol. 137, Issue 1, 96-100 [Cited in related U.S. Appl. No. 14/062,165].
Brogden, "alpha-Methyl-p-tyrosine: a review of its pharmacology and clinical use", Drugs, Feb. 1981, 21(2), 81-89 [Cited in related U.S. Appl. No. 14/062,165].
Cabrera Lopez et al., "Effects of rapamycin on angiomyolipomas in patients with tuberous sclerosis", Nefrologia, Apr. 2011, 31(3), 292-298 [Cited in related U.S. Appl. No. 14/062,165].
Chen, "Progress in the development of bestatin analogues as aminopeptidases inhibitors", Current Medical Chemistry, Mar. 2011, vol. 18, No. 7, 964-976 [Cited in related U.S. Appl. No. 14/062,165].
Chhun et al., "7. The Cytochrome P-450 2C9/2C19 but Not the ABCB1 Genetic Polymorphism May Be Associated With the Liver Cytochrome 3A4 Induction by Phenytoin", Journal of Clinical Psychopharmacology, Jun. 2012, vol. 32, No. 3, 429-431 [Cited in related U.S. Appl. No. 14/062,165].
Chiu et al., "Lipid-Based Nanoparticulate Systems for the Delivery of Anti-Cancer Drug Cocktails: Implications on Pharmacokinetics and Drug Toxicities", Current Drug Metabolism, 2009, 10, 861-874 [Cited in related U.S. Appl. No. 14/062,165].
De Kort et al., "Leaky gut and diabetes mellitus: what is the link?", Obesity Reviews, 2011, 12, 449-458 [Cited in related U.S. Appl. No. 14/062,165].
Dorr et al., "Evaluation of melanotan-II, a superpotent cyclic melanotropic peptide in a pilot phase-I clinical study", Life Sciences, Apr. 1996, vol. 58, Issue 20, 1777-1784 [Cited in related U.S. Appl. No. 14/062,165].
Ell, "Brain tumor uptake of iodo-alpha-methyl-tyrosine", Journal of Nuclear Medicine, Nov. 1991, 32(11), 2193-2194 [Cited in related U.S. Appl. No. 14/062,165].
Espeillac et al., "S6 kinase 1 is required for rapamycin-sensitive liver proliferation after mouse hepatectomy", The Journal of Clinical Investigation, Jul. 2011, 121(7), 2821-2832 [Cited in related U.S. Appl. No. 14/062,165].
Fan et al., "Impact of system L amino acid transporter 1 (LAT1) on proliferation of human ovarian cancer cells: a possible target for combination therapy with anti-proliferative aminopeptidase inhibitors", Biochemical Pharmacology, Sep. 15, 2010, vol. 80, Issue 6, 811-818 [Cited in related U.S. Appl. No. 14/062,165].
Fitzgerald et al., "Effect of Melanotan, [Nle(4), D-Phe(7)]-alpha-MSH, on melanin synthesis in humans with MC1R variant alleles", Peptides, Feb. 2006, vol. 27, Issue 2, 388-394 [Cited in related U.S. Appl. No. 14/062,165].
Fujimori et al., Mechanisms of Hyperglycemic Response to Chlorpromazine Administered into Lateral Ventricle in Rats-I, Possible Role of Dopaminergic Nervous System, Neuropharmacology, Pergamon Press, Oxford, vol. 13, No. 4, Apr. 1974 [Cited in related U.S. Appl. No. 15/695,327].
Chimura et al., "Immunohistochemical expression of aminopeptidase N (CD13) in human lung squamous cell carcinomas, with special reference to Bestatin adjuvant therapy", Pathology International, Jun. 2006, vol. 56, Issue 6, 296-300 [Cited in related U.S. Appl. No. 14/062,165].
Kargiotis et al., "Epilepsy in the cancer patient", Cancer Chemotherapy and Pharmacology, Mar. 2011, vol. 67, No. 3, 489-501 [Cited in related U.S. Appl. No. 14/062,165].
Krige et al., "CHR-2797: An antiproliferative aminopeptidase inhibitor that leads to amino acid deprivation in human leukemic cells", Cancer Research, Aug. 15, 2008, 68(16), 6669-6679 [Cited in related U.S. Appl. No. 14/062,165].
Kulke et al., "Future directions in the treatment of neuroendocrine tumors: consensus report of the National Cancer Institute Neuroendocrine Tumor clinical trials planning meeting", Journal of Clinical Oncology, Mar. 2011, vol. 29, No. 7, 934-943 [Cited in related U.S. Appl. No. 14/062,165].

Landmark, "Antiepileptic Drugs in Non-Epilepsy Disorders—Relations between Mechanisms of Action and Clinical Efficacy", CNS Drugs, 2008, 22, 1, 27-47 [Cited in related U.S. Appl. No. 14/062,165].
Liu et al., "Combinatorial effects of lapatinib and rapamycin in triple-negative breast cancer cells", Molecular Cancer Therapeutics, Aug. 2011, 10, 1460-1469 [Cited in related U.S. Appl. No. 14/062,165].
Longhurst et al., "Effects of Catecholamine Depletion with AMPT (alpha-methyl-para-tyrosine) in Obsessive-Compulsive disorder", Biological Psychiatry, Elsevier Science, NY, vol. 46, No. 4, Aug. 1999, pp. 573-576 [Cited in related U.S. Appl. No. 15/695,327].
Longo et al., "Efficacy and tolerability of long-acting octreotide in the treatment of thymic tumors: results of a pilot trial", American Journal of Clinical Oncology, Apr. 2012, 35(2), 105-109 [Cited in related U.S. Appl. No. 14/062,165].
Nakagami, "A case of malignant pheochromocytoma treated with 131I-metaiodobenzylguanidine and alpha-methyl-p-tyrosine", Japanese Journal of Medicine, May-Jun. 1990, vol. 29, No. 3, 329-333 [Cited in related U.S. Appl. No. 14/062,165].
Ram et al., "Failure of alpha-methyltyrosine to prevent hypertensive crisis in pheochromocytoma", Archives of Internal Medicine, Nov. 1985, vol. 145, No. 11, 2114-2115 [Cited in related U.S. Appl. No. 14/062,165].
Russo "Correlation Between Hepatocyte Growth Factor (HGF) and Gamma-Aminobutyric Acid (GABA) Plasma Levels in Autistic Children", Biomarker Insights, Jun. 1, 2013, pp. 69-75 [Cited in related U.S. Appl. No. 15/138,733].
Ryakhovsky et al.," The first preparative solution phase synthesis of melanotan II", Beilstein Journal of Organic Chemistry, 2008, 4, 1-6 [Cited in related U.S. Appl. No. 14/062,165].
Standards of Medical Care in Diabetes—2013, American Diabetes Association, Jan. 2013, vol. 36, Supp. 1, S11-S66 [Cited in related U.S. Appl. No. 14/062,165].
Steinsapir et al., "Metyrosine and pheochromocytoma", Archives of Internal Medicine, Apr. 1997, vol. 157, No. 8, 901-906 [Cited in related U.S. Appl. No. 14/062,165].
Tada, "Three cases of malignant pheochromocytoma treated with cyclophosphamide, vincristine, and dacarbazine combination chemotherapy and alpha-methyl-p-tyrosine to control hypercatecholaminemia", Hormone Research, Jan. 1998, vol. 49, No. 6, 295-297 [Cited in related U.S. Appl. No. 14/062,165].
Taveria-Dasilva, "Sirolimus therapy in patients with lymphangioleiomyomatosis", Summaries for patients, Annals of Internal Medicine, Jun. 21, 2011, 154(12), 144 [Cited in related U.S. Appl. No. 14/062,165].
Terauchi et al., "Inhibition of APN/CD 13 leads to suppressed progressive potential in ovarian carcinoma cells", BMC Cancer, 2007, 7, 1-12 [Cited in related U.S. Appl. No. 14/062,165].
Tsukamoto et al., "Aminopeptidase N (APN)/CD13 inhibitor, Ubenimex, enhances radiation sensitivity in human cervical cancer", BMC Cancer, Mar. 2008, 8:74, 8 pages [Cited in related U.S. Appl. No. 14/062,165].
Voorhess, "Effect of alpha-methyl-p-tyrosine on 3,4-dihydroxyphenylalanine (DOPA) excretion of hamsters with melanotic melanoma", Cancer Research, Mar. 1968, 28, 452-454 [Cited in related U.S. Appl. No. 14/062,165].
Yamada et al., "Involvement of Adrenaline in Diazepam-Induced Hyperglycemia in mice" Life Sciences, Pergarmon Press, Oxford, vol. 66, No. 13, Feb. 18, 2000 [Cited in related U.S. Appl. No. 15/695,327].
Zimmermann et al., "Prolonged Inhibition of Presynaptic Catecholamine Synthesis With .alpha.-Methyl-Para-Tyrosine Attenuates the Circadian Rhythm of Human TSH Secretion" J. Soc. Gynecol Investing, May/Jun. 2001, vol. 8 No. 3, 174-178 [Cited in related U.S. Appl. No. 14/062,165].
Ziying et al., Observation of Cabamazepine Treating Painful Diabetic Neuropathy, Medical Recapitulate, vol. 15, Issue 8, pp. 1270-1271, Apr. 30, 2009 [Cited in related U.S. Appl. No. 15/695,327].
Sumida et al., Jpn. J. Clin. Pharmacol Ther., vol. 31, No. 2, Mar. 2000, pp. 305-306 [Cited in related U.S. Appl. No. 16/693,589].
He et al.,"Cytoplasm-predominant Pten associates with increased region-specific brain tyrosine hydroxylase and dopamine D2 recep-

(56) References Cited

OTHER PUBLICATIONS tors in mouse model with autistic traits" Molecular Autism, vol. 6, No. 63, 2015, 10 Pages [Cited in related U.S. Appl. No. 16/693,589].

Kato, "Intestinal First-Pass Metabolism of CYP3A4 Substrates" Drug Metab. Pharmacokinet., vol. 23, No. 2, pp. 87-94, 2008 [Cited in related U.S. Appl. No. 16/693,589].

* cited by examiner

COMPOSITION AND METHODS FOR TREATING INTESTINAL HYPERPERMEABILITY

CROSS-REFERENCE TO RELATED APPLICATIONS

This application is a continuation of U.S. patent application Ser. No. 16/693,589, filed Nov. 25, 2019, which is a continuation of U.S. patent application Ser. No. 16/112,879, now U.S. Pat. No. 10,517,845, filed Aug. 27, 2018, which is a continuation of U.S. patent application Ser. No. 15/695,327, now U.S. Pat. No. 10,085,959, filed Sep. 5, 2017, which is a continuation of U.S. patent application Ser. No. 15/138,733, now U.S. Pat. No. 9,757,348, filed on Apr. 26, 2016, which is a continuation of U.S. patent application Ser. No. 14/520,116, now U.S. Pat. No. 9,326,962, filed on Oct. 21, 2014, which is a continuation-in-part of U.S. patent application Ser. No. 14/062,165, filed on Oct. 24, 2013, now abandoned, which claims the benefit of U.S. Patent Application No. 61/894,261, filed on Oct. 22, 2013, the entireties of which are incorporated by reference herein.

TECHNICAL FIELD

The present inventions relate generally to compositions, kits, and methods for the treatment of intestinal hyperpermeability.

BACKGROUND

The intestinal epithelium separates luminal contents from the interstitium. This function is primarily determined by the integrity of the epithelium and the tight junction that seals the paracellular space. These intestinal tight junctions are selectively permeable. This permeability can be increased physiologically in response to the presence of luminal nutrients. Permeability can also be increased pathologically by mucosal immune cells and cytokines, the enteric nervous system, and by pathogens. It is believed to be critical that the intestinal mucosa prevent potentially dangerous contents of the intestinal lumen, including the microorganisms that reside there from entering internal areas and the systemic circulation. There are several clinical conditions, both intestinal and systemic, that are associated with compromised intestinal barrier function.

A possible link between intestinal hyperpermeability and disease has been proposed. This has led to a sharp increase in the diagnosis of intestinal hyperpermeability, also known as "leaky gut syndrome." Diseases that have been correlated with intestinal hyperpermeability include diabetes, autism, fibromyalgia, inflammatory bowel disease (IBD), graft versus host disease (GVHD), HIV/AIDS, multiple organ dysfunction syndrome, irritable bowel syndrome (IBS), celiac disease, eczema, psoriasis, acute pancreatitis, Parkinson's disease, depression, chronic fatigue syndrome, asthma, multiple sclerosis, arthritis, ankylosing spondylitis, nonalcoholic fatty liver disease, alcoholic cirrhosis, environmental enteropathy, and kwashiorkor. It is believed that restoration of the intestinal barrier will improve or cure the underlying disease. Several drug targets that could potentially promote barrier restoration have been proposed, but none have proven safe and effective.

Thus, there remains a need for the development of safe and effective treatments or cures for intestinal hypersensitivity and numerous underlying diseases.

SUMMARY

The present invention provides methods, compositions, and kits for treating intestinal hyperpermeability in a subject in need thereof, including underlying conditions including hyperglycemia, and including underlying diseases such as diabetes, autism, fibromyalgia, inflammatory bowel disease (IBD), graft versus host disease (GVHD), HIV/AIDS, multiple organ dysfunction syndrome, irritable bowel syndrome (IBS), celiac disease, eczema, psoriasis, acute pancreatitis, Parkinson's disease, depression, chronic fatigue syndrome, asthma, multiple sclerosis, arthritis, ankylosing spondylitis, nonalcoholic fatty liver disease, alcoholic cirrhosis, environmental enteropathy, or kwashiorkor. In certain embodiments, the invention provides methods comprising administering to a subject in need thereof an effective amount of a tyrosine hydroxylase inhibitor. In certain embodiments, the invention provides methods comprising administering to a subject in need thereof an effective amount of a tyrosine hydroxylase inhibitor and a p450 3A4 promoter.

In other embodiments, the invention provides pharmaceutical compositions comprising a tyrosine hydroxylase inhibitor and a p450 3A4 promoter. Also provided are kits comprising a tyrosine hydroxylase inhibitor and a p450 3A4 promoter together with packaging for same.

DETAILED DESCRIPTION OF ILLUSTRATIVE EMBODIMENTS

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment incudes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder. This condition, disease or disorder can be intestinal hyperpermeability.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with respect to the particular compound, component or composition selected, the route of administration, and the ability of the components to elicit a desired result in the individual, but also with respect to factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide improved therapeutic response. An effective amount is also one in which any toxic or detrimental effects of the components are outweighed by the therapeutically beneficial effects.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"High blood glucose level" is used interchangeably with "hyperglycemia" herein and is defined as a fasting plasma blood glucose level of 126 mg/dl or greater on two separate occasions, Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein can be prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein that contain, for example, both amino and carboxy groups, also include reference to their corresponding zwitterions.

The term "stereoisomers" refers to compounds that have identical chemical constitution, but differ as regards the arrangement of the atoms or groups in space. The term "enantiomers" refers to stereoisomers that are mirror images of each other that are non-superimposable.

The term "administering" means either directly administering a compound or composition of the present invention, or administering a prodrug, derivative or analog which will form an equivalent amount of the active compound or substance within the body.

The terms "subject," "individual," and "patient" are used interchangeably herein, and refer to an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

The term "inhibitor" as used herein includes compounds that inhibit the expression or activity of a protein, polypeptide or enzyme and does not necessarily mean complete inhibition of expression and/or activity. Rather, the inhibition includes inhibition of the expression and/or activity of a protein, polypeptide or enzyme to an extent, and for a time, sufficient to produce the desired effect.

The term "promoter" as used herein includes compounds that promote the expression or activity of a protein, polypeptide or enzyme and does not necessarily mean complete promotion of expression and/or activity. Rather, the promotion includes promotion of the expression and/or activity of a protein, polypeptide or enzyme to an extent, and for a time, sufficient to produce the desired effect.

While not intending to be bound by any particular mechanism of operation, it is believed that the tyrosine hydroxylase inhibitors according to the present invention function by decreasing the amount of adrenaline secreted into the bloodstream.

Methods of treating intestinal hyperpermeability in a subject are provided. Such methods can include administering to a subject in need thereof an effective amount of a tyrosine hydroxylase inhibitor. Other such methods include administering to a subject in need thereof an effective amount of tyrosine hydroxylase inhibitor and a p450 3A4 promoter. This tyrosine hydroxylase inhibitor and the p450 3A4 promoter can be administered simultaneously.

Administration of the tyrosine hydroxylase inhibitor or the tyrosine hydroxylase inhibitor and the p450 3A4 promoter can be through various routes, including orally, nasally subcutaneously, intravenously, intramuscularly, transdermally, vaginally, rectally or in any combination thereof. Transdermal administration can be effected using, for example, oleic acid, 1-methyl-2-pyrrolidone, dodecyl-nonaoxyethylene glycol monoether.

In other suitable embodiments of the invention the tyrosine hydroxylase inhibitor and the p450 3A4 promoter are administered during a cycle consisting of five to seven days of administering the tyrosine hydroxylase inhibitor and the p450 3A4 promoter, and one to two days of not administering the tyrosine hydroxylase inhibitor and the p450 3A4 promoter. In some suitable embodiments of the invention, at least six of said cycles of administration are performed. In some suitable embodiments of the invention, 25 mg of the tyrosine hydroxylase inhibitor is administered.

In certain embodiments, the tyrosine hydroxylase inhibitor is a tyrosine derivative. The tyrosine derivative can be capable of existing in different isomeric forms, including stereoisomers and enantiomers. The tyrosine derivative can, for example, exist in both L-form or D-form. The tyrosine derivative can, for example, also exist in a racemic form. Representative tyrosine derivatives include one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine methyl ester hydrochloride, H-3,5-diiodo-tyrosine methyl ester hydrochloride, H-D-3,5-diiodo-tyrosine methyl ester hydrochloride, H-D-tyrosine methyl ester hydrochloride, D-tyrosine methyl ester hydrochloride, D-tyrosine-methyl ester hydrochloride, methyl D-tyrosinate hydrochloride, H-D-tyrosine methyl ester·hydrochloride, D-tyrosine methyl ester hydrochloride, H-D-tyrosine methyl ester-hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5-I2)-OSu, Fmoc-tyrosine(3-NO2)-OH, α-methyl-L-tyrosine, α-methyl-D-tyrosine, and α-methyl-DL-tyrosine. In certain embodiments of the invention, the tyrosine derivative is α-methyl-L-tyrosine. In other embodiments, the tyrosine derivative is α-methyl-D-tyrosine. In other embodiments, the tyrosine derivative is α-methyl-DL-tyrosine in a racemic form.

In methods of the invention, 60 mg of the tyrosine derivative is administered orally and 0.25 mL of a 2 mg/mL suspension of the tyrosine derivative is administered subcutaneously.

Representative p450 3A4 promoters include 5,5-diphenylhydantoin, valproic acid and carbamazepine. In a suitable embodiment of the invention, the composition includes 5 mg to 25 mg of 5,5-diphenylhydantoin. Representative subjects include mammals. In certain embodiments, the mammal is a human.

In some embodiments of the invention, methods further comprising assessing progression of said intestinal hyperpermeability in said subject are provided. This assessing step can be performed before said administering step or after said administering step.

Representative conditions that can be treated with methods of the present invention include hyperglycemia. Symptoms of the condition hyperglycemia can include: polyphagia, polydipsia, polyuria, blurred vision, fatigue (sleepiness), weight loss, poor wound healing (cuts, scrapes, etc.), dry mouth, dry or itchy skin, tingling in feet or heels, erectile dysfunction, recurrent infections, external ear infections (swimmer's ear), cardiac arrhythmia, stupor, coma, and seizures. Representative diseases that can be treated with methods of the present invention include diabetes, autism, fibromyalgia, inflammatory bowel disease (IBD), graft versus host disease (GVHD), HIV/AIDS, multiple organ dysfunction syndrome, irritable bowel syndrome (IBS), celiac disease, eczema, psoriasis, acute pancreatitis, Parkinson's disease, depression, chronic fatigue syndrome, asthma, multiple sclerosis, arthritis, ankylosing spondylitis, nonalcoholic fatty liver disease, alcoholic cirrhosis, environmental enteropathy, or kwashiorkor.

Administration of pharmaceutically active molecules such as inhibitor and/or promoters can be through various routes, including orally, nasally, subcutaneously, intravenously, intramuscularly, transdermally, vaginally, rectally or in any combination thereof. Transdermal administration can be effected using, for example, oleic acid, 1-methyl-2-pyrrolidone, dodecylnonaoxyethylene glycol monoether.

The tyrosine hydroxylase inhibitor can be administered during a cycle consisting of five to seven days of administering the tyrosine hydroxylase inhibitor, and one to two days of not administering the tyrosine hydroxylase inhibitor. The tyrosine hydroxylase inhibitor can be administered over the course of at least six said cycles. In one suitable embodiment of the invention, the tyrosine hydroxylase inhibitor is administered daily. In another suitable embodiment of the invention, the tyrosine hydroxylase inhibitor is administered multiple times per day.

Representative treatment methods according to the invention comprise administering to a subject in need thereof an effective amount of a tyrosine hydroxylase inhibitor or a tyrosine hydroxylase inhibitor and a p450 3A4 promoter are provided.

Suitable embodiments can include a pharmaceutical composition comprising a tyrosine hydroxylase inhibitor and a p450 3A4 promoter. The tyrosine hydroxylase inhibitor can be a tyrosine derivative.

Also provided herein are kits comprising a tyrosine hydroxylase inhibitor and a p450 3A4 promoter together with packaging for same. The tyrosine hydroxylase inhibitor can be a tyrosine derivative. The tyrosine derivative can include tyrosine derivatives capable of existing in isomeric form. The tyrosine derivatives can include tyrosine derivatives in its L-form or in its D-form. The tyrosine derivative can, for example, also exist in a racemic form. Representative tyrosine derivatives include one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine-methyl ester hydrochloride, H-3,5-diiodo-tyrosine-methyl ester hydrochloride, H-D-3,5-diiodo-tyrosine-methyl ester hydrochloride, H-D-tyrosine-methyl ester hydrochloride, D-tyrosine methyl ester hydrochloride, D-tyrosine-ome hydrochloride, methyl D-tyrosinate hydrochloride, H-D-tyrosine-methyl ester·hydrochloride, D-tyrosine methyl ester hydrochloride, H-D-tyrosine-methyl ester-hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5-I2)-OSu, Fmoc-tyrosine(3-NO2)-OH, α-methyl-L-tyrosine, α-methyl-D-tyrosine, and α-methyl-DL-tyrosine. In certain embodiments of the invention, the tyrosine derivative is α-methyl-L-tyrosine. In other specific embodiments of the invention, the tyrosine derivative is α-methyl-D-tyrosine. In other embodiments, the tyrosine derivative is α-methyl-DL-tyrosine in a racemic form.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

EXAMPLE 1

Two-hundred patients were initially screened. Thirty subjects meeting the study criteria consented. Nine (9) subjects had high blood glucose levels (hyperglycemia) prior to consenting to the study.

A high blood glucose level (hyperglycemia) is defined as a fasting plasma blood glucose level of 126 mg/dl or greater on two separate occasions, The average patient age was sixty-two years old and the median patient age was sixty years old. Six of the patients were female and three of the patients were male. Five of the patients were fifty to sixty years old and four of the patients were over the age of sixty.

The patients in the study were administered a treatment regimen that included a tyrosine hydroxylase inhibitor (i.e., α-methyl-DL tyrosine), a melanin promoter (i.e., melanotan II), a p450 3A4 promoter (i.e., 5,5-diphenylhydantoin), and a leucine aminopeptidase inhibitor (i.e., N-[(2S,3R)-3-amino-2-hydroxy-4-phenylbutyryl]-L-leucine). These compounds were administered on each of five days per week for a period of six weeks, with one or two days off between weekly cycles. Blood glucose level was monitored for all subjects biweekly. Blood glucose levels were determined by daily blood glucose tests followed-up with laboratory blood glucose tests every two weeks.

After approximately two to four weeks, all nine of the subjects had normal blood glucose levels defined as a fasting plasma blood glucose level of 125 mg/dl or lower on two separate occasions.

Overall, the above-noted treatment was well tolerated by the subjects, with no adverse events related to the treatment, and responses have been documented to the treatment 100%.

What is claimed is:

1. A method of treating multiple sclerosis comprising administering to a subject in need thereof an effective amount of a tyrosine hydroxylase inhibitor that is at least one of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine (tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine-methyl ester hydrochloride, H-3,5-diiodo-tyrosine-methyl ester hydrochloride H-D-3,5-diiodo-tyrosine-methyl ester hydrochloride, H-D-tyrosine methyl ester hydrochloride, D-tyrosine methyl ester hydrochloride, methyl D-tyrosinate hydrochloride, D-tyrosine methyl ester hydrochloride, (2R)-2-amino-3-(4 hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5-I$_2$)-OSu, Fmoctyrosine(3-NO$_2$)—OH, α-methyl-L-tyrosine, a-methyl-D-tyrosine, and α-methyl DL-tyrosine.

2. The method of claim 1 further comprising administering a p450 3A4 promoter.

3. The method of claim 2 wherein the tyrosine hydroxylase inhibitor and the p450 3A4 promoter are administered simultaneously.

4. The method of claim 2 wherein the tyrosine hydroxylase inhibitor and the p450 3A4 promoter are administered orally, subcutaneously, intravenously, transdermally, vaginally, rectally or in any combination thereof.

5. The method of claim 4 wherein the transdermal administration is performed in combination with oleic acid, 1-methyl-2-pyrrolidone, or dodecylnonaoxyethylene glycol monoether.

6. The method of claim 1 wherein the tyrosine hydroxylase inhibitor and the p450 3A4 promoter are administered during a cycle consisting of five to seven days of administering the tyrosine hydroxylase inhibitor and the p450 3A4 promoter, and one to two days of not administering the tyrosine hydroxylase inhibitor and the p450 3A4 promoter.

7. The method of claim 6 that includes at least six of said cycles.

8. The method of claim 1 comprising administering α-methyl-D-tyrosine to said subject.

9. The method of claim 1 comprising administering α-methyl-DL-tyrosine in a racemic form to said subject.

10. The method of claim 1 wherein 60 mg of the tyrosine derivative is administered orally and 0.25 mL of a 2 mg/mL suspension of the tyrosine derivative is administered subcutaneously.

11. The method of claim 2 wherein the p450 3A4 promoter is 5, 5-diphenylhydantoin.

12. The method of claim 2 wherein the p450 3A4 promoter is valproic acid or carbamazepine.

13. The method of claim 1 wherein the subject is a human.

* * * * *